United States Patent

Jacquot et al.

[11] Patent Number: 5,243,088
[45] Date of Patent: Sep. 7, 1993

[54] 1-MONODEBROMINATION OF DIBROMONAPHTHALENE COMPOUNDS

[75] Inventors: Roland Jacquot, Sainte Foy Les Lyons; Francoise Truchet, Lyons, both of France

[73] Assignee: Potasse et Produits Chimiques, Thann, France

[21] Appl. No.: 786,076

[22] Filed: Oct. 31, 1991

[30] Foreign Application Priority Data

Oct. 31, 1990 [FR] France .................. 90 13512

[51] Int. Cl.$^5$ .................. C07C 39/38; C07C 41/24
[52] U.S. Cl. .................. 568/656; 560/139; 568/737; 570/204
[58] Field of Search .............. 560/139; 568/656, 737; 570/204

[56] References Cited

U.S. PATENT DOCUMENTS 4,827,057 5/1989 Kaesbauer et al. .......... 570/204

FOREIGN PATENT DOCUMENTS 0179447 4/1986 European Pat. Off. .

OTHER PUBLICATIONS

Streitwieser et al., in *Introduction to Organic Chemistry*, 1976, pp. 1050–1053.

*Primary Examiner*—Marianne M. Cintins
*Assistant Examiner*—Michael B. Hydorn
*Attorney, Agent, or Firm*—Burns, Doane, Swecker & Mathis

[57] ABSTRACT

Dibromonaphthalene compounds having the formula (1):

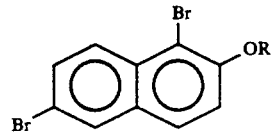

are 1-monodebrominated by reacting same, neat or in an acid organic solvent, with molecular hydrogen or a compound that generates nascent hydrogen, in situ, in the medium of reaction, in the presence of a catalytically effective amount of a hydrodebromination catalyst.

21 Claims, No Drawings

1-MONODEBROMINATION OF DIBROMONAPHTHALENE COMPOUNDS

BACKGROUND OF THE INVENTION

1. Field of the Invention

The present invention relates to the debromination of dibromonaphthalene compounds and, more especially, to the monodebromination of dibromonaphthalene compounds having the formula:

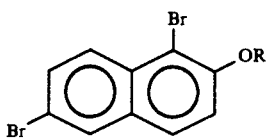

(1)

wherein R is hydrogen, an alkyl, aryl, aralkyl or

radical, with R' itself being an alkyl radical, by regio-selective catalytic hydrodebromination.

The final products of such debromination reaction thus have the formula:

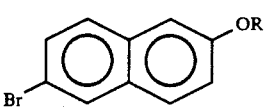

(2)

in which R is as defined above.

2. Description of the Prior Art

The 6-bromonaphthalenes of formula (2) above are known and valuable compounds. For example, 6-bromo-2-methoxynaphthalene is widely used for synthesizing naproxen or nabumetone, two pharmaceuticals which are well known for their therapeutic anti-inflammatory properties, and also for synthesizing methallenestril, which is an estrogen (compare *The Merck Index*, eleventh edition, pages 1002, 1014 and 937 (1989)).

As regards 6-bromo-2-hydroxynaphthalene (also referred to as 6-bromo-β-naphthol), this is principally used for synthesizing the aforesaid 6-bromo-2-methoxynaphthalene via alkylation by means of dimethyl sulfate or methanol.

According to EP-A-179,447, 6-bromo-2-[hydroxy or alkoxy]naphthalenes may be prepared by stoichiometric metallic reduction of the corresponding 1,6-dibromo-2-[hydroxy or alkoxy]naphthalenes by the following reaction:

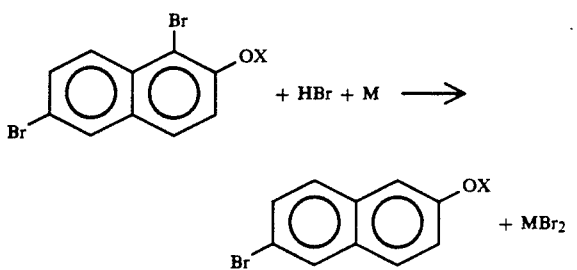

in which X is hydrogen or an alkyl radical, and M is a reducing metal such as iron or tin. The above dibrominated compounds may themselves be simply prepared by direct bromination of the corresponding non-brominated compounds:

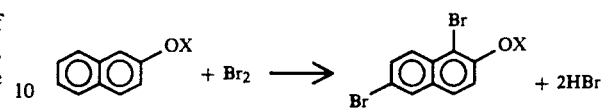

However, reducing dibrominated derivatives of naphthalene to monobrominated derivatives by a method as described above presents the disadvantage, inter alia, of requiring large amounts of metal, which metal is ultimately present in the reaction effluent which is difficult to salvage and often becomes a pollutant, such as FeBr$_2$.

Moreover, the yield of the desired monobrominated compounds from such a process may prove to be inadequate.

SUMMARY OF THE INVENTION

Accordingly, a major object of the present invention is the provision of improved process for debrominating certain dibrominated naphthalene compounds, firstly to avoid the above disadvantages and drawbacks to date characterizing the state of this art, and, secondly, to provide a high-yield regio-selective debromination, particularly in position 1.

Briefly, the present invention features the debromination of dibromonaphthalene compounds, comprising reacting (i) a dibrominated naphthalene compound of the formula:

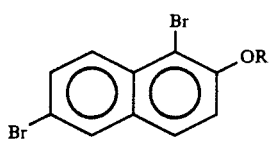

(1)

wherein R is hydrogen, an alkyl, aryl, aralkyl or

radical, with R' itself being an alkyl radical, with (ii) molecular hydrogen or a compound adopted to produce nascent hydrogen in the medium of reaction, either neat or in an organic acid solvent, in the presence of a catalytically effective amount of a hydrodebromination catalyst.

DETAILED DESCRIPTION OF THE PREFERRED EMBODIMENTS OF THE INVENTION

More particularly according to the present invention, it will be seen that the subject process presents a variety of advantages and great flexibility. First, it avoids the stoichiometric consumption of reducing metals. Another unexpected and surprising advantage is that it is also highly selective, in the sense that when the compounds of formula (1) are reacted, only the bromine atom in position 1 is substituted, and this transpires even in the event that a large stoichiometric excess of hydrogen is used. Too, the yields of the monobrominated compounds are high.

The reaction may be carried out employing a wide range of pressures and temperatures and under a variety of other reaction conditions. Thus, it may be carried out neat or in appropriate solvent medium, and the catalysis thereof may be of the homogeneous, supported homogeneous or heterogeneous type.

The catalyst is recovered and recycled in all instances, thus making the process more economical. It may be a batch, semi-continuous or continuous process, carried out in an agitated reactor or a trickling fixed bed. A final advantage of the process of the invention is that it can be applied directly, without any preliminary separation or purification, to the reaction product obtained by direct bromination of a non-brominated naphthalene compound which is substituted at the 2-position by an OR radical and thus provides the desired dibrominated starting material.

The catalytic reaction involved in the process of the invention may be of the homogeneous or heterogeneous type. It is considered as homogeneous when the catalyst is soluble in the reaction medium (monophase liquid system) and heterogeneous when the catalyst is in a solid form, insoluble in that medium (an at least diphase, liquid/solid system). In the event of a homogeneous catalyst, two possibilities exist. First, the reaction medium may be diphase (liquid/liquid), if the catalyst is in the form of a water-soluble complex and the dibrominated compound is in organic solution, immiscible with water. A reaction of this type is described, in particular, in U.S. Pat. No. 4,925,990 for the hydrogenation of $\alpha,\beta$-unsaturated aldehydes. This technique makes it easy to recycle the catalyst.

The second possibility is for the reaction medium again to be monophase, with only one liquid phase; in this event, as one means for recycling the catalyst, the monobrominated compound obtained is precipitated by cooling it, and the catalyst is maintained in solution. The catalytic solution can then easily be recycled. According to the invention, it is advantageous to operate under conditions of heterogeneous catalysis, particularly as this greatly facilitates subsequent recovery of the catalyst: it is effected by simple means, such as filtration or decantation.

The hydrodebromination catalysts employed in the process of the invention are catalysts which are per se known to this art. They have been described, particularly, in the following texts: *Catalytic Hydrogenation over Platinum Metals.* P. N. Rylander, Academic Press (1967) and *Practical Catalytic Hydrogenation (Techniques and Applications)*, M. Freifelder, Wiley Intersciences (1971). The function of the catalysts is to permit a bromine atom borne by an aromatic carbon to be substituted by a hydrogen atom. Such catalysts generally comprise an active phase based on precious metals such as at least one of the following: platinum, palladium, rhodium, irridium, ruthenium or osmium. The active phase may comprise a mixture of these elements. According to the invention, it is preferable to use an active phase based on rhodium or palladium.

In the event of homogeneous catalysis, the catalytically active element or elements may be in the metallic state or in the form of a salt which is soluble in the reaction medium.

In the event of heterogeneous catalysis, catalysts comprising an active phase deposited onto a carrier substrate are generally used. The carrier may be of the monolithic substrate type (honeycomb or other forms), or may be in a divided or particulate form. The term "divided or particulate form" refers to pulverulent products (powders) and also articles obtained by shaping these products (spheres, tablets, pellets, granules, extrusions, agglomerates and others, of circular, oval, trilobal or multilobal section, either solid or hollow).

Carriers of the type including spheres, tablets, etc., present the advantage of providing catalysts which can subsequently be separated from the reaction medium very rapidly, simply by decantation. Catalysts of the pulverulent type generally require a filtering stage to separate them.

The supported catalysts may contain from 0.1% to 90% by weight of precious metals relative to the total weight of catalyst, and generally from 0.5% to 5%.

Exemplary carriers, whether used alone or mixed, include activated carbons; oxides such as silica, alumina, aluminosilicates, titanium dioxide, magnesium oxide or zirconium oxide; zeolites; or ceramics such as silicon carbide or nitride.

All of the above carriers are of course selected with a specific surface area suitable for catalytic applications.

The preferred catalysts for carrying out the process of the invention are those comprising a catalytic phase based on palladium and/or rhodium, deposited onto a carrier of the activated carbon or pulverulent alumina type.

According to the invention, the reaction may be carried out neat or in a solvent medium. In a preferred embodiment of the invention, it is carried out in a solvent medium. It has been determined that the selection of the solvent to be used is particularly important, and that the choice must be limited to organic solvents and, more preferably, to acid organic solvents.

By "acid organic solvents" are intended either (a) protic organic solvents selected from among the simple or functionalized carboxylic acids, or (b) aprotic organic solvents containing at least one organic or inorganic acid.

Indeed, it has been found that protic organic solvents of the alcohol type are not suitable for carrying out the process of the invention.

Exemplary carboxylic acids which are suitable solvents for the process of the invention include methanoic, ethanoic, propanoic, butanoic and trifluoroacetic acid. The term "carboxylic acids" of course also comprehends simple or functionalized polycarboxylic acids, which too are quite suitable.

Particularly suitable aprotic organic solvents include:

(i) aromatic hydrocarbons, especially benzene and the alkylbenzenes (ethyl-, butyl- and propylbenzene, etc.), toluene and the xylenes;

(ii) paraffinic and cycloparaffinic hydrocarbons, especially the $C_5$-$C_{20}$ alkanes (iso- and n-pentane, hexane, etc.); alkylalkanes (2,2-dimethylbutane, 2,3-dimethylbutane, 2-methylpentane, 3-methylpentane, 2,4-dimethylpentane, 2,3-dimethylpentane, 2,2,4-trimethylpentane, 2,3,4-trimethylpentane, 3-methylhexane, 2,2,5-trimethylhexane, etc.); cycloalkanes (cyclopentane, cyclohexane, etc.); and alkylcycloalkanes (methylcyclopentane, 1,1-dimethylcyclopentane, 1,2- and 1,3-dimethylcyclopentane, methylcyclohexane, ethylcyclohexane, isopropylcyclohexane, etc.);

(iii) halogenated and particularly fluorinated and chlorinated hydrocarbons of paraffinic, cycloparaffinic and aromatic compounds such as those indicated above, especially dichloromethane, 1,2-dichloroethane and chlorobenzene;

(iv) esters, particularly acetates and benzoates, especially alkyl esters, for example ethyl acetate and methyl benzoate;
(v) ethers, particularly dimethoxyethane; and
(vi) amides, particularly N-methylpyrolidone.

It will of course be appreciated that the solvent may comprise either mixtures of carboxylic acids, mixtures of aprotic organic solvents, or mixtures of carboxylic acids with aprotic organic solvents.

Exemplary acids which may be included, either alone or mixed, in aprotic organic solvents such as those indicated above, comprise:
(i) among the inorganic acids, nitric, phosphoric or sulfuric acid or halide acids such as hydrochloric or hydrobromic;
(ii) among the organic acids, the carboxylic acids indicated above, methanesulfonic, triflic, ethanesulfonic or benzenesulfonic acid.

The amount, in mols, of acid contained in the aprotic organic solvent generally ranges from 0.1 to 5 times the amount in mols of dibrominated derivatives used, and preferably from 0.8 times to twice that amount.

The proportion of catalyst used is not critical and may vary widely; generally, from 0.01% to 50% by weight of catalyst is used relative to the dibrominated derivative, and preferably from 0.1% to 10%.

The amount of hydrogen used may also vary widely; nevertheless, it must at least correspond to the stoichiometric amount required for complete substitution of half the bromine atoms provided in the form of the initial dibrominated compound. There is no upper limit on this amount.

According to the invention, the hydrogen is preferably provided in a gaseous molecular form ($H_2$). Nascent hydrogen may be used equally as well, namely, hydrogen which is formed in situ in the reaction medium via decomposition of a precursor compound such as a formate or formic acid.

The temperatures used to carry out the reaction may vary very widely. In the case of a reaction neat, they range from the melting point of the dibrominated derivative to a temperature not exceeding the decomposition point of said derivative and/or of the reaction product.

In the case of a reaction carried out in a solvent medium, temperature ranging from room temperature, theoretically up to the boiling point of the solvent may be used, although care must again be taken not to exceed temperatures at which the debrominated derivative and/or the reaction product might decompose; in practice, temperatures ranging from 20° to 200° C., and preferably from 50° to 150° C., are employed.

The reaction may be carried out either at atmospheric pressure in an open-type reactor, or in a trickling fixed bed into which a continuous stream of hydrogen is bubbled, or preferably under autogenous pressure in a closed reactor of the autoclave type, containing a hydrogen atmosphere. In this latter event, the hydrogen pressure may range from 1 to 50 bars and preferably from 5 to 20 bars.

The reaction is preferably carried out with agitation, generally until the complete or quasi-complete consumption of the dibrominated naphthalene compound introduced as a reagent.

When the reaction is complete, the monobrominated compound obtained is separated from the reaction medium by any means per se known to this art, for example by filtering, decanting, centrifuging, extraction or distillation. Depending upon whether the process is carried out in homogeneous or heterogeneous phase, in bulk or in a solvent medium, recovery of the monobrominated compound may entail conducting one or more of the aforesaid separations. In the event of a reaction carried out in heterogeneous phase in a solvent medium, for example, the catalysts will first be recovered, particularly by filtering or decanting, then the monobrominated compound and organic solvent phase will be separated, for example by extraction with water or distillation.

The catalysts and/or solvents thus recovered can then be recycled to the beginning of the process, optionally after being purified. As regards the monobrominated compound recovered, this may be subjected to additional purifying stages, if necessary.

It will be appreciated that the process of the invention is particularly applicable to starting dibrominated compounds in which R is hydrogen or an alkyl radical, with a view to producing corresponding compounds monobrominated in the δ position.

In order to further illustrate the present invention and the advantages thereof, the following specific examples are given, it being understood that same are intended only as illustrative and nowise limitative.

In said examples to follow, TT is the conversion rate, i.e., the ratio:

$$\frac{\text{quantity in mols of dibrominated compound converted}}{\text{quantity in mols of dibrominated compound introduced}} \times 100$$

RR is the yield of the reaction relative to a given reaction product, i.e., the ratio:

$$\frac{\text{quantity in mols of product formed}}{\text{quantity in mols of dibrominated compound introduced}} \times 100$$

RT is the selectivity of the reaction for a given product; it is defined by the ratio RR/TT.

EXAMPLE 1

9 mg of a hydrodebromination catalyst comprising activated carbon coated with 5% by weight of palladium, 1.2 g of 1,6-dibromo-2-naphthol, and 15 ml of 1,2-dichloroethane containing 0.6 g of trifluoromethanesulfonic acid (acid organic solvent) were introduced into a 35 ml glass flask.

The open flask was placed in a 125 ml autoclave (Hastellay C). The autoclave was purged twice with nitrogen at a pressure of 10 bars. 20 bars of hydrogen were then introduced, and heating was applied for 10 hours at 100° C., with agitation.

Analysis by gas phase chromatography with an internal standard provided the following results:

TT = 95%
6-bromo-2-naphthol RT = 70%

EXAMPLE 2

9 mg of a catalyst comprising an alumina powder coated with 5% by weight of rhodium, 15 ml of 1,2-dichloroethane containing 0.002 mol of HBr, and 1.2 g of 1,6-dibromo-2-naphthol were introduced into a 35 ml glass flask.

The procedure of Example 1 was repeated, except that the heating at 100° C. was only maintained for 4 hours.

GPC analysis provided the following results:

TT = 39%
6-bromo-2-naphthol RT = 90%

EXAMPLE 3

20 mg of a catalyst comprising activated carbon coated with 2.5% by weight of rhodium, 1.2 g of 1,6-dibromo-2-naphthol, and 15 ml of acetic acid were introduced into a 35 ml glass flask.

The procedure of Example 2 was then repeated. GPC analysis provided the following results:

TT = 99%
6-bromo-2-naphthol RT = 92%

EXAMPLE 4

10 mg of palladium acetate, 1.2 g of 1,6-dibromo-2-naphthol, and 15 ml of acetic acid were introduced into a 35 ml glass flask.
The procedure of Example 2 was then repeated.
GPC analysis provided the following results:

TT = 95%
6-bromo-2-naphthol RT = 88%

EXAMPLE 5

45 mg of a catalyst comprising activated carbon coated with 3% by weight of palladium, 1.3 g of 1,6-dibromo 2-methoxynaphthalene, and 15 ml of acetic acid were introduced into a 35 ml glass flask.
The procedure of Example 2 was then repeated.
HPLC analysis provided the following results:

TT = 95%
6-bromo-2-methoxynaphthalene RR = 57%
6-bromo-2-naphthol RR = 28%
Total RT for 6-isomers 89%

COMPARATIVE EXAMPLE 6

10 mg of palladium acetate, 1.2 g of 1,6-dibromo-2-naphthol, and 15 ml of ethanol were introduced into a 35 ml glass flask.
The procedure was then repeated.
GPC analysis provided the following results:

TT = 95%
1-bromo-2-naphthol RR = 17%
2-naphthol RR = 66%
6-bromo-2-naphthol RR = 0%

COMPARATIVE EXAMPLE 7

15 mg of a catalyst comprising activated carbon coated with 3% by weight of palladium, 1.26 g of 1,6-dibromo-2-methoxynaphthalene, and 15 ml of methanol were introduced into a 35 ml glass flask.
The procedure of Example 2 was then repeated.
HPLC analysis provided the following results:

TT = 95%
1-bromo-2-methoxynaphthalene RR = 81%
6-bromo-2-methoxynaphthalene RR = 0%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the regioselective 1-monodebromination of a dibromonaphthalene compound having the formula (1):

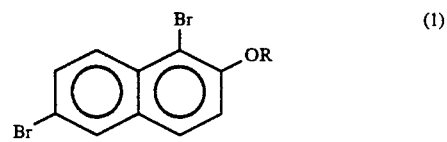

wherein R is a hydrogen atom, an alkyl radical, an aryl radical, an aralkyl radical or —CO—R' radical, in which R' is an alkyl radical, comprising reacting, neat or in an acid organic solvent, the dibromonaphthalene compound (1) with molecular hydrogen or a compound that generates nascent hydrogen, in situ, in the medium of reaction, in the presence of a catalytically effective amount of a hydrodebromination catalyst, so as to provide a product having high selectivity of 6-monobrominated products compared to 1-monobrominated products.

2. The process as defined by claim 1, wherein formula (1), R is a hydrogen atom or an alkyl radical.

3. The process as defined by claim 1, carried out neat.

4. The process as defined by claim 1, carried out in an acid organic solvent medium.

5. The process as defined by claim 4, said acid organic solvent comprising a simple or functionalized carboxylic or polycarboxylic acid.

6. The process as defined by claim 4, said acid organic solvent comprising an aprotic organic solvent containing an organic or inorganic acid.

7. The process as defined by claim 6, said aprotic organic solvent comprising an aromatic hydrocarbon, paraffinic or cycloparaffinic hydrocarbon, halogenated hydrocarbon, ester, ether or amide.

8. The process as defined by claim 4, said acid organic solvent comprising a simple or functionalized carboxylic or polycarboxylic acid, methane-, ethane- or benzenesulfonic acid, or triflic acid.

9. The process as defined by claim 6, said inorganic acid comprising nitric, sulfuric, phosphoric or a hydrohalide acid.

10. The process as defined by claim 6, wherein the amount, in mols, of said organic or inorganic acid ranges from 0.1 to 5 times the amount in mols of said dibromonaphthalene compound (1).

11. The process as defined by claim 10, said amount, in mols, of said organic or inorganic acid ranges from 0.8 to 2 times the amount of dibromonaphthalene compound (1).

12. The process as defined by claim 1, said hydrodebromination catalyst comprising a platinum, palladium, rhodium, iridium, ruthenium or osmium active phase, alone or in admixture thereof.

13. The process as defined by claim 12, said active phase being deposited onto a carrier substrate.

14. The process as defined by claim 13, said carrier substrate being in a divided form.

15. The process as defined by claim 14, said carrier substrate comprising activated carbon, an oxide, a zeolite or a ceramic.

16. The process as defined by claim 15, said carrier substrate comprising activated carbon or alumina.

17. The process as defined by claim 1, comprising reacting said dibromonaphthalene compound (1) with molecular hydrogen.

18. The process as defined by claim 1, comprising reacting said dibromonaphthalene compound (1) with a compound that generates nascent hydrogen, in situ, in the medium of reaction.

19. The process as defined by claim 18, comprising reacting said dibromonaphthalene compound (1) with formic acid or a formate.

20. The process as defined by claim 1, carried out under superatmospheric pressure.

21. The process as defined by claim 1, said dibromonaphthalene compound (1) comprising the reaction product of the direct bromination of a naphthalene compound having the formula:

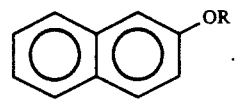

* * * * *